United States Patent [19]

Asai et al.

[11] Patent Number: 4,735,693
[45] Date of Patent: Apr. 5, 1988

[54] PROCESS FOR PRODUCING CARBON FIBER

[75] Inventors: Hajime Asai; Fujio Nakao, both of Ohtake, Japan

[73] Assignee: Mitsubishi Rayon Co., Ltd., Tokyo, Japan

[21] Appl. No.: 899,797

[22] Filed: Aug. 26, 1986

Related U.S. Application Data

[63] Continuation-in-part of Ser. No. 733,881, May 14, 1985, abandoned.

[30] Foreign Application Priority Data

May 18, 1984 [JP] Japan .................. 59-99759
May 18, 1984 [JP] Japan .................. 59-99760

[51] Int. Cl.$^4$ .................................. G01N 27/50
[52] U.S. Cl. ............................ 204/1 T; 423/460
[58] Field of Search ........... 204/130, 231, 1 T, 433, 204/28, 56 R, 1 K; 423/460

[56] References Cited

U.S. PATENT DOCUMENTS

| | | | |
|---|---|---|---|
| 2,895,888 | 7/1959 | Varner | 204/28 |
| 3,437,568 | 4/1969 | Hasselmann et al. | 204/3 |
| 3,759,805 | 9/1973 | Chapman et al. | 204/130 |
| 3,859,187 | 1/1975 | Druin et al. | 204/130 |
| 4,050,997 | 9/1977 | Heissler et al. | 204/28 |
| 4,234,398 | 11/1980 | Yamamoto | 204/130 |
| 4,401,533 | 8/1983 | Saito et al. | 204/130 |
| 4,500,840 | 2/1985 | Galwey et al. | 204/231 X |

FOREIGN PATENT DOCUMENTS

| | | | |
|---|---|---|---|
| 93695 | 9/1974 | Japan | 204/130 |
| 1297946 | 11/1972 | United Kingdom | 204/130 |
| 1326736 | 8/1973 | United Kingdom | 204/28 |

OTHER PUBLICATIONS

Dietz and Peover, Journal of Materials Science, (1971), pp. 1441–1446.
Theodoridou I, J. Electroanal. Chem. 122, (1981), pp. 67–61.
Theodoridou II, J. Electroanal. Chem. 124, (1981), pp. 87–94.
Jannakoudakis, Zeitschrift fur Physikalische Chemie Neue Folge, Bd. 136, (1980), pp. 225–230.
Theodoridou III, Synthetic Metals 9, (1984), pp. 19–30.
Jannakoudakis II, Synthetic Metals 11, (1985), pp. 101–108.
Bensenhard, Revue de Chimie Minerale, 19, (1982), pp. 588–601.
Proctor, Carbon 21, (1983), pp. 53–59.
Mentus, The 16th Biennial Conference on Carbon, (1983), pp. 359–360.

*Primary Examiner*—G. L. Kaplan
*Attorney, Agent, or Firm*—Oblon, Fisher, Spivak, McClelland & Maier

[57] ABSTRACT

A method for detecting the surface characteristic of a carbon fiber, which comprises making the carbon fiber travel through an electrolyte solution, applying an electric potential in said solution between the carbon fiber serving as a working electrode and a counter electrode provided in the solution, said potential being varied continuously within a range of potential not higher than the standard electrode potential, and detecting continuously the resulting charnge of intensity of electric current, and a process for producing a carbon fiber giving a high interfacial bond strength between the fiber and matrix resin, which comprises making the carbon fiber have a constant surface characteristic by application of the above-mentioned detection method.

4 Claims, 3 Drawing Sheets

PROCESS FOR PRODUCING CARBON FIBER

This application is a continuation-in-part, of application Ser. No. 733,881, filed May 14, 1985 and now abandoned.

FIELD OF THE INVENTION

This invention relates to a novel process for surface treatment of carbon or graphite fibers, so as to obtain constant conditions of surface state by detecting surface characteristics of carbon or graphite fibers by potential sweeping technique of electrochemistry.

BACKGROUND ART

The most important factor for exhibiting the inherent strength of a carbon fiber in composite materials is a high interfacial bond strength between the fiber and matrix resin. Particularly, with increasingly higher tensile strength of carbon fibers, the energy released at fracture increases and as a result a high interfacial bond strength corresponding thereto becomes necessary. Further, a high carbonization temperature is necessary to obtain high modulus carbon fibers, as a result making the surface of the carbon fibers inactive. Consequently, it becomes necessary for higher performance carbon fibers to have the controlled interfacial bond strength.

To meet the above-mentioned necessities, it is a common practice to activate the surface of carbon fibers, as proposed for example in Japanese Patent Application Kokoku (Post-Exam Publn) No. 20033/80, by introducing functional groups with various surface treatments such as electrolytic oxidation or gas-phase oxidation, or by increasing the specific surface caused by physical etching. As carbon fibers of the higher performance are used, such surface treatments become more complex.

In general, the optimum level of surface treatment is determined based on some relationship between the surface treatment conditions and the mechanical properties of composites. However, even when the surface treatment conditions are kept constant, the surface state of the fiber can vary due to unexpected external disturbances such as variation of starting fiber and carbonization conditions. Consequently, there is always the danger of variation of composite properties.

Accordingly, it is not sufficient for controlling the properties of composite merely to keep the surface treatment conditions constant. Basically, it is necessary to control the surface state always to a constant condition.

Physical and chemical surface characteristics of carbon fibers are affected by surface treatment and as a result exert a great influence on the composite properties. In order to know clearly the surface treatment levels optimum for mechanical properties of a composite, it is necessary to grasp fully the surface state. Although there have been many examples of surface state analysis for carbon fibers such as measurement of the specific surface area by gas adsorption or analysis of functional groups by titration, ESCA and the like, they are no more than analytical studies in research stage, so these techniques are practically incapable of usage in industrial quality control.

In the prior art, no method was known for controlling surface treatment levels directly by measuring surface characteristics (as opposed to just the surface area) of carbon fibers. There was simply no available measuring method exhibiting a high enough correlation with the mechanical properties of the carbon fiber, and which could also be adapted to continuous measurement during carbon fiber manufacture. Two known measuring methods of surface characteristics are ESCA (EXPS) (electron spectroscopy for chemical analysis) and the BET (Brunauer-Emmett-Teller) method (for surface area measurement), but it is impossible to incorporate these methods into a process for carbonization of carbon fibers. The present invention makes this possible by applying a measuring method based on a new observation correlating surface characteristics of the fiber with certain electrochemical measurements.

OBJECT OF THE INVENTION

The present inventors have made extensive studies to develop a method which enables, in a production line of carbon fibers, adjustment of the surface treatment conditions and as a result control of the surface characteristics. As a result, a practical method of detection has been developed which can give continuously precise knowledge of the surface characteristics of carbon fibers which can be correlated well with the properties of composites. Thus, the present invention has been accomplished.

The first object of this invention is to adapt the surface analysis of carbon fibers to product inspection in plants. The second object is to conduct the process control of surface treatment by incorporating the surface analysis directly into the production line.

BRIEF DESCRIPTION OF THE DRAWINGS

There is given below a brief description of the drawings which will be referred to to illustrate the construction of this invention.

CONSTRUCTION OF THE INVENTION

Figure 1:
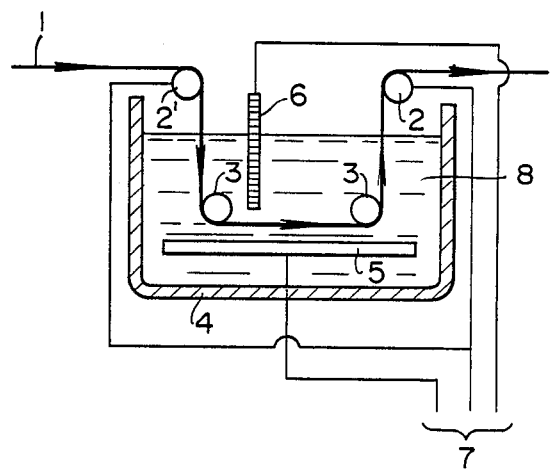
FIGS. 1 and 2 show each an example of apparatuses suitable for practicing this invention. The numbers in the Figures indicate the following.
 1 Carbon fiber
 2 Electrically conductive roll
 3 Electrically nonconductive guide pulley
 4 electrolyte solution bath
 5 Counter electrode
 6 Reference electrode
 7 Connecting terminal to function generator, potentiostat and X-Y recorder
 8 Electrolyte solution

The essentials of this invention lie in making a carbon fiber or a graphite fiber travel through an electrolyte solution, applying an electric potential in said solution between the carbon fiber or graphite fiber serving as the working electrode and the counter electrode provided in the solution, said potential being varied continuously within a potential range not higher than the standard electrode potential, and detecting continuously the resulting change in current intensity, and further in producing a carbon fiber or graphite fiber while controlling the preceding step so that the detected current intensity may be kept constant.

This invention is based on the application of the potential sweep method of electrochemistry in which the change of electric current produced by potential sweep is measured by using cyclic voltammetry, differential pulse polarography or alternating-current polarography. It is an analytical technique widely used for electrochemical evaluation of electrodes and analysis of electrode reactions.

There have been many attempts to use carbon fibers in electrodes. Further, there are known some examples wherein the potential sweep method was applied to chemical modification of carbon-fiber electrodes or analysis of graphite intercalation compounds.

After formation of an intercalation compound generally in the presence of sulfuric acid, the potential sweep method is carried out and this serves to detect crystal structures on the surface layer of the carbon fiber. On the other hand, in the present invention, by changing the sulfuric acid solution to a solution which does not form an intercalation compound with the carbon fiber, what is detected by the potential sweep method is an increase in the number of functional groups on the surface layer of the carbon fiber in addition to an increase of surface area. According to this invention, this type of measurement is highly correlated with the mechanical properties (particularly interfacial bond strength between the fiber and the matrix resin) of the composite carbon fiber.

However, there has not yet been known any example wherein the electric current intensity obtained by the potential sweep method was investigated in relation to mechanical properties of carbon fiber composites, and the existence of such correlation has been revealed only after extensive study of the present inventors. Though the details of how the electric current intensity obtained by the potential sweep method is related to the surface characteristic of carbon fibers are not known, it can be assumed that it is a characteristic which corresponds to the concentration of functional groups participating in the oxidation-reduction reaction on the surface and to the physical surface area thereof. As is clear from page 37, FIGS. 2-19 of "Electrochemistry of Biological Molecules" Glenn Dryhurst, ACADEMIC PRESS London (1977), in the potential sweep method, as in the process according to the present invention, capacitive current and faradaic current may both be measured. As applied to measurements of the surface of a carbon fiber, the capacitive current corresponds to an increase of surface area, and the faradaic current corresponds to an increase in the number of functional groups. If faradaic current is not measured, the correlation with mechanical properties will not be as high, and such a method would be unsuitable for the purposes of this invention. On the other hand, the measurement of $\Delta q_m$ as reported by R. Dietz, M. E. Peover in the Journal of Materials Science 6 (1971) 1441-1446 is carried out using an apparatus which is quite different from that of the present invention, and accordingly only the capacitive current is measured, meaning that only an increase in the surface area is detected. As clarified above, according to the present invention, the mechanical properties of the carbon fiber are dependent upon the number of functional groups on the surface much more so than the increase in surface area. Only a measurement according to the present invention (including a measurement of the faradaic current) can provide reliable information leading to adequate control of mechanical properties of the carbon fibers. This sophisticated feature was not recognized at all in the prior art. Aside from the details, the current intensity obtained by the potential sweep method is in good correspondence to the mechanical properties of the composite as is clearly shown also in Examples described later, and hence can be considered an index indicating the interfacial bond strength. Thus the interfacial strength of composites can be best exhibited by controlling the index.

An outline of the process according to this invention will be described below.

Subsequent to the surface treatment, an electrolyte solution bath 4 as shown, for example, in FIG. 1 is provided, to which is attached an analyzer for a potential sweep method represented typically by cyclic voltammeter, differential pulse polarograph or alternating-current polarograph.

Any of these common electrochemical detection apparatuses may be used in potential sweep. For example, cyclic voltammetry can be achieved by connecting a carbon fiber as the working electrode, a Ag/AgCl electrode as the reference electrode and a platinum electrode as the counter electrode to a potentiostat to which a function generator and a recorder have been connected.

This invention will be described below in more detail.

Figure 2:
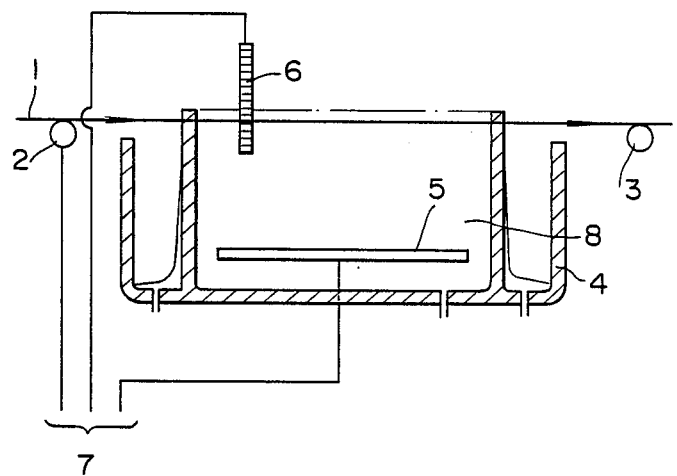

Examples of a measuring apparatus suitable for practicing this invention are shown in FIGS. 1 and 2. Any type of apparatus may be used so long as it permits measurement using a carbon fiber as the working electrode.

The carbon fiber specimen has to be passed through an electrolyte solution so as to give a constant electrode surface area. The fiber may be in the form of single tow, or plural tows passed simultaneously. When a continuous fiber is passed through the solution, it is brought in contact with a conductive roll outside the electrolytic bath to apply a potential to the carbon fiber. In this case, the conductive roll may be single, or two or more rolls may be used positioned on the both sides of the electrolytic bath. Further, the length of the specimen may be controlled either by immersing the carbon fiber in the electrolytic solution by using non-conductive guide pulleys as shown in FIG. 1 or by immersing the fiber by utilizing the overflow of electrolytic solution as shown in FIG. 2.

The counter electrode should be of enough surface area not to cause errors in the measurement.

As the reference electrode, there can be used, for example, a saturated calomel electrode or a Ag/AgCl electrode.

Basically, any electrolyte solution may be used in this invention so long as it permits passage of electricity, provided that it does not form an intercalation compound with the carbon fiber as does concentrated sulfuric acid. Preferable examples of the electrolyte include potassium chloride, sodium nitrate, phosphoric acid and sodium hydroxide. The concentration of the electrolyte is preferably in the range of 1 to 20% and the pH should be controlled at a fixed value. In this invention 5% aqueous phosphoric acid was used as the standard for convenience.

As to the electrode part, a continuous carbon fiber tow 1 traveling through the electrolyte bath is contacted with a roll 2 and is given thereby an electric current to serve as the working electrode, and potential sweep is conducted by using a platinum electrode 5 as the counter electrode and a Ag/AgCl electrode as the reference electrode 6.

The potential range should be set within a range not exceeding the standard electrode potential of the electrolyte solution. Further, since the electric current intensity is dependent on the potential sweep rate, it should be maintained constant. The pH of electrolytic solution also should be kept constant throughout the measurement. The electric current density at a certain fixed potential vs. Ag/AgCl reference electrode, at +0.4 V in this invention, is detected by plotting a current-potential curve on the X-Y recorder.

The current intensity per unit area, ipa as defined below, instead of the apparent current intensity, i, is not affected by the number of tows nor the length of specimens.

Here $$ipa(\mu A/cm^2) = i/\text{Total surface area of the tow,}$$

wherein the total surface area of the two was calculated from the sample weight, number of monofilaments, weight per unit length of the tow and density of the carbon fiber.

The potential sweep test is more preferably carried out before the sizing treatment than after it, because of fluctuation of effective surface area or of necessity of washing off the electrolyte.

The carbon fiber tow after measurement is passed through the water bath to eliminate the electrolyte, dried, and then subjected to sizing treatment.

Though the main object of this invention is to conduct the process control of surface treatment by incorporating potential sweep apparatus directly into the production line, this invention can also be conducted off line to product inspection of carbon fibers.

The carbon fiber specimen can be in any form including tow, sheet, cloth and paper so long as it can keep the shape as an electrode. Further, resins such as sizing agents can be adhering to the specimen. In this case, however, since the effective surface area decreases a correction therefor is necessary.

The carbon fibers referred to in this invention are not limited to those of PAN-type; they include also those of pitch-type and cellulose-type; further they may be graphite fibers obtained by treating at higher temperatures.

The carbon fiber or graphite fiber used in practicing this invention is preferably subjected beforehand to surface oxidation treatment by means of a dry or wet process. However, such surface treatment is not always necessary. For example, this invention can be satisfactorily applied to the untreated fiber of 24 t/mm² modulus to determine the mechanical properties of its composite.

EXAMPLE

This invention will be described below with reference to Examples.

EXAMPLE 1

Figure 3:
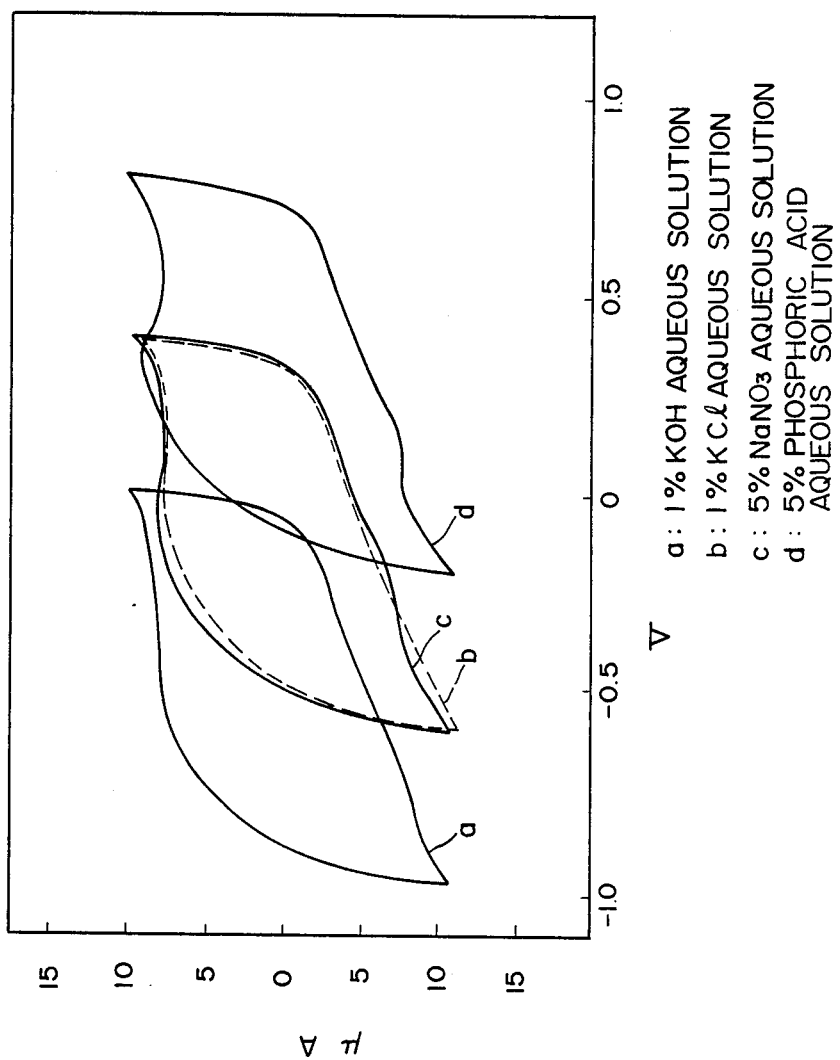
FIG. 3 is a graph showing variation of the current potential curve observed with the change of the kind of electrolyte solution of this invention.

Cyclic voltammetry, one potential sweep method, of an unsized carbon fiber tow of 6,000 fils., Pyrofil T-1 (a trade name, mfd. by Mitsubishi Rayon Co., Ltd.) was measured using the apparatus shown in FIG. 1. In this example the tow was fixed with the conductive rolls and kept in stationary state as the working electrode during the measurement. A platinum electrode was used as the counter electrode and the potential of the working electrode was measured in contrast to a Ag/AgCl reference electrode. These electrodes were connected to a Hokuto Denko type HA-301 potentiostat and automatic potential sweep programs were carried out on a custom built function generator Hokuto Denko type HB-104. Potential sweep was performed at the contact scanning rate 2 mv/sec over the potential range −0.2 to +0.8 V in various kinds of aqueous electrolyte solution shown in Table 1. After scanning 3 times or more until they became stable, current-potential curves were plotted on the X-Y recorder as seen in FIG 3. The figure of cyclic voltammograms did not change substantially with electrolyte, but only shifted to the lower voltage side as increasing pH of the solution, as is well known in general.

TABLE 1

| Exp. No. | Electrolyte solution | pH | Potential range (V) |
|---|---|---|---|
| 1 | 5% aq. phosphoric acid | 2 | −0.2~+0.8 |
| 2 | 1% aq. KCl solution | 7 | −0.6~+0.4 |
| 3 | 5% aq. NaNO₃ solution | 7 | −0.6~+0.4 |
| 4 | 1% aq. KOH solution | 14 | −1.0~0 |

EXAMPLE 2

Cyclic voltammetry was carried out in a similar manner in Example 1 besides varying the scanning rate in 5% aqueous phosphoric acid solution. Current intensity, i, was read off at +0.40 V selected as the standard voltage of the cyclic voltammogram and ipa was calculated, defined by the following equation, in which the total surface area of the tow was calculated from the sample weight, number of monofilaments, weight per unit length of the tow and density of the carbon fiber. In this example these values were 0.020 g, 6000 fils, 0.400 g/m and 1,800 g/cm³ respectively.

$$ipa\ (\mu A/cm^2) = i/\text{Total surface area of the tow}$$

The ipa at same scanning rates in cyclic voltammetry changed in linear proportion to scanning rate, as is seen in Table 2.

TABLE 2

| Exp. No. | Scanning rate (mV/sec) | ipa ($\mu A/cm^2$) |
|---|---|---|
| 5 | 0.2 | 0.020 |
| 6 | 2 | 0.190 |
| 7 | 20 | 1.880 |

EXAMPLE 3

Cyclic voltammetry of carbon fiber tows was carried out continuously in the apparatus shown in FIG. 1. The tows were contacted via the conductive roll, serving as the working electrode into the electrolyte solution bath. The tows were then passed through a water bath to eliminate electrolyte sticking to the fiber surface and finally wound on a spool. At the constant speed of 1 m/min, cyclic voltammograms were obtained in a similar manner to Example 2, wherein the sweep rate was kept constant at 2 mV/sec. The number and the length of the tows inside the electrolyte were varied by changing the distance between the guide pulleys as indicated in Table 3, which the values of ipa calculated are on approximately the same level with each other irrespective of the sample size.

TABLE 3

| Exp. No. | Number of tows (12K) | Length of tows inside the electrolyte (cm) | ipa ($\mu A/cm^2$) |
| --- | --- | --- | --- |
| 8 | 1 | 20 | 0.191 |
| 9 | 1 | 40 | 0.181 |
| 10 | 10 | 40 | 0.202 |
| 11 | 200 | 50 | 0.198 |

EXAMPLE 4

An expoxy sized tow in place of an unsized tow was treated in the same manner as in Example 3, wherein the length of the tow inside the electrolyte was held at 20 cm.

As shown in Table 4, the ipa is seen to decrease approximately linearly with increasing sizing agent ahead. This is because the effective surface area had been decreased due to the adhered sizing agent.

TABLE 4

| Exp. No. | Amount of sizing agent (%) | ipa ($\mu A/cm^2$) |
| --- | --- | --- |
| 12 | 0 | 0.195 |
| 13 | 0.5 | 0.181 |
| 14 | 2.0 | 0.165 |

EXAMPLE 5

A PAN-based carbon fiber tow having Young's modulus of 25 t/mm$^2$ was oxidized in air at 400° C. to 800° C. for 2 minutes to effect surface treatment.

The tow then was passed into the electrolyte bath to determine ipa continuously in the same manner as in Example 3. Then the tow was passed into a water bath to eliminate electrolyte, a dryer and a sizing treatment bath and was wound on a spool.

Tensile strength of the carbon fiber obtained was measured in strand according to JIS-R-7601 and to estimate interfacial bond strength between the carbon fiber and the matrix resin, transverse flexural strength of the fiber reinforced epoxy composites was measured as follows.

Unidirectional model composites were made by the pre-preg technique. Pre-pregs were made by impregnating the carbon fibers with Pyrofil 320 epoxy resin (a trade name, mfd. by Mitsubishi Rayon Co., Ltd.).

Prepregs cut in the proper size were put in a mould and kept in a hot press. Pressure was applied when the resin had just started gelling so as to keep the fiber volume to 60 to 65% in the composite. Curing condition was at 130° C. for 3 hours and 6 test pieces 60 mm×10 mm×2 mm in size were cut out.

Flexural strength was measured by the three-points bending technique in the transverse direction to the fiber axis using span-to-thickness ratio of the composites of 15:1 according to ASTM D-790.

The treated tow consisted of 12,000 fils and weighed 0.805 g/m and the fiber density was 1.790 g/cm$^3$.

Table 5 shows the air oxidation temperature, ipa, tensile strength and transverse flexural strength.

The optimum oxidation treatment temperatures for tensile strength and those for transverse flexural strength were different in their range from each other and it can be seen that interfacial bond strength of composites is well reflected in ipa.

TABLE 5

| Exp. No. | Air oxidation temp. (°C.) | ipa ($\mu A/cm^2$) | Tensile strength (kg/mm$^2$) | Transverse flexural strength (kg/mm$^2$) |
| --- | --- | --- | --- | --- |
| 15 | 400 | 0.155 | 370 | 9.8 |
| 16 | 600 | 0.233 | 390 | 11.4 |
| 17 | 800 | 0.379 | 320 | 12.5 |

EXAMPLE 6

PAN-based carbon fibers were carbonized at 1200° C. after being preoxidized at various temperature and then were electrochemically oxidized in aqueous phosphoric acid solution for 30 seconds to effect surface treatment. The level of treatment was varied by changing the current density at the electrolytic oxidation.

The treated fiber tow was passed into the electrolyte bath to measure ipa continuously in the same manner as in Example 3 and finally wound on a spool.

Table 6 lists the current density at surface treatment, ipa, and mechanical properties of the composites. As is evident from the Table, ipa is in good correspondence to interfacial strength of the composites, because the carbon fibers pre-oxidized at different temperature have different transverse flexural strength even though electrochemically oxidized at the same current density.

TABLE 6

| Exp. No. | Current density at electrolytic oxidation (A/m$^2$) | ipa ($\mu A/cm^2$) | Tensile strength (kg/mm$^2$) | Transverse flexural strength (kg/mm$^2$) |
| --- | --- | --- | --- | --- |
| 18 | 0.8 | 0.248 | 460 | 11.1 |
| 19 | 0.8 | 0.259 | 390 | 12.0 |
| 20 | 0.8 | 0.373 | 330 | 12.3 |
| 21 | 1.2 | 0.521 | 320 | 13.4 |
| 22 | 0.08 | 0.187 | 370 | 10.1 |

EXAMPLE 7

PAN-based carbon fiber having 28 ton/mm$^2$ modulus was subjected to electrolytic oxidation in 5% aqueous sodium nitrate solution for 30 seconds at several current densities to effect surface treatment.

The middle modulus carbon fiber tow was subsequently passed through the electrolyte bath for cyclic voltammetry measurement and then washed, dried, coated with sizing agent and finally wound around a spool.

The tow contained 6,000 monofilaments and weighed 0.785 g/m and the fiber density was 1.775 g/cm$^3$.

Table 7 shows surface treatment level, ipa and mechanical properties of the composites. Here, ILSS of the composites as same as Example 5 was measured using short-beam method with a span to thickness ratio of 5:1.

TABLE 7

| Exp. No. | Current density (A/m$^2$) | ipa ($\mu A/cm^2$) | ILSS (kg/mm$^2$) | Transverse flexural strength (kg/mm$^2$) |
| --- | --- | --- | --- | --- |
| 23 | 0 | 0.05 | 6.5 | 7.2 |
| 24 | 0.4 | 0.08 | 7.2 | 8.3 |
| 25 | 0.8 | 0.12 | 8.1 | 10.2 |
| 26 | 1.5 | 0.23 | 8.8 | 11.5 |

TABLE 7-continued

| Exp. No. | Current density (A/m²) | ipa (μA/cm²) | ILSS (kg/mm²) | Transverse flexural strength (kg/mm²) |
| --- | --- | --- | --- | --- |
| 27 | 3.1 | 0.49 | 9.1 | 9.5 |

EXAMPLE 8

The same middle modulus carbon fiber as that of Example 7 was surface treated in 5% aqueous ammonium carbonate solution.

Table 8 shows the current density of electrolytic treatment, ipa of the tow, ILSS and transverse flexural strength of the composites.

Comparing Table 8 with Table 7, the relation between current density and ipa changes greatly but that between ipa and composite properties is not changeable but constant.

TABLE 8

| Exp. No. | Current density (A/m²) | ipa (μA/cm²) | ILSS (kg/mm²) | Transverse flexural strength (kg/mm²) |
| --- | --- | --- | --- | --- |
| 28 | 0 | 0.05 | 6.5 | 7.5 |
| 29 | 1.5 | 0.13 | 7.6 | 8.0 |
| 30 | 4.5 | 0.18 | 8.8 | 9.0 |
| 31 | 9.5 | 0.22 | 9.2 | 10.5 |
| 32 | 15.5 | 0.21 | 9.2 | 11.0 |
| 33 | 31.0 | 0.25 | 9.1 | 11.5 |

EXAMPLE 9

The carbon fiber having a modulus of 25 ton/mm² was further heat treated at 1800° C. to 2000° C. for radius residence time to obtain the carbon fiber having equal modulus of 30 ton/mm².

The surface treatment of the middle modulus carbon fiber tow was performed in air at 400° C. to 800° C. for 2 minutes. After oxidation, the two was treated in the same manner as in Example 3.

Table 9 gives the results of ipa and composite properties of the carbon fibers obtained.

From these results one can conclude that ipa reflects well the surface characteristics and is in good correspondence to interfacial strength of the composite.

In this example, the tow with 12,000 mono-filaments weighted 0.715 to 0.740 g/m and the fiber density was 1.74 to 1.76 g/cm³.

TABLE 9

| Exp. No. | Heat treatment temp. (°C.) | Surface treatment temp. (°C.) | ipa (μA/cm²) | Transverse flexural strength (kg/mm²) |
| --- | --- | --- | --- | --- |
| 34 | 1800 | 600 | 0.222 | 9.8 |
| 35 | 1900 | 400 | 0.068 | 8.2 |
| 36 | " | 600 | 0.174 | 9.7 |
| 37 | " | 800 | 0.254 | 10.6 |
| 38 | 2000 | 600 | 0.142 | 8.8 |

EXAMPLE 10

The carbon fibers carbonized at various temperatures were further heat-treated at 2500° C. for changing to graphite fibers of 40 ton/mm² modulus.

The electrolytic oxidation of the graphite fiber tow was carried out in aqueous phosphoric acid solution at 1.0 A/m² for 20 seconds.

The two was passed into the electrolyte bath to measure ipa continuously, then washed and finally wound.

Table 10 shows the modulus of the starting carbon fibers and graphite fibers obtained, ipa and the transverse flexural strength of the composites.

As seen from Table 10, even when graphite fibers have the same modulus of 40 ton/mm², they can have varied surface characteristics and composite properties depending on the modulus of starting carbon fibers. The tow consisted of 12,000 filaments and had a weight per unit length of 0.725 g/m and the density of the graphite fiber was 1.81 g/cm³.

TABLE 10

| Experiment No. | Modulus of elasticity of starting fiber (t/mm²) | Modulus of elasticity of graphite fiber (t/mm²) | ipa (μA/cm²) | Lateral bending strength (kg/mm²) |
| --- | --- | --- | --- | --- |
| 39 | 21 | 39 | 0.158 | 8.1 |
| 40 | 23 | 40 | 0.136 | 8.0 |
| 41 | 25 | 40 | 0.077 | 6.3 |

EXAMPLE 11

Carbon fibers of 6K having a modulus of elasticity of 30 ton/mm² were heated in air at various temperatures to carry out an oxidizing treatment of the surface.

In the same manner as in Example 5, ipa, ILSS and transverse flexural strength of the composite were measured of samples of the fibers.

Figure 4:
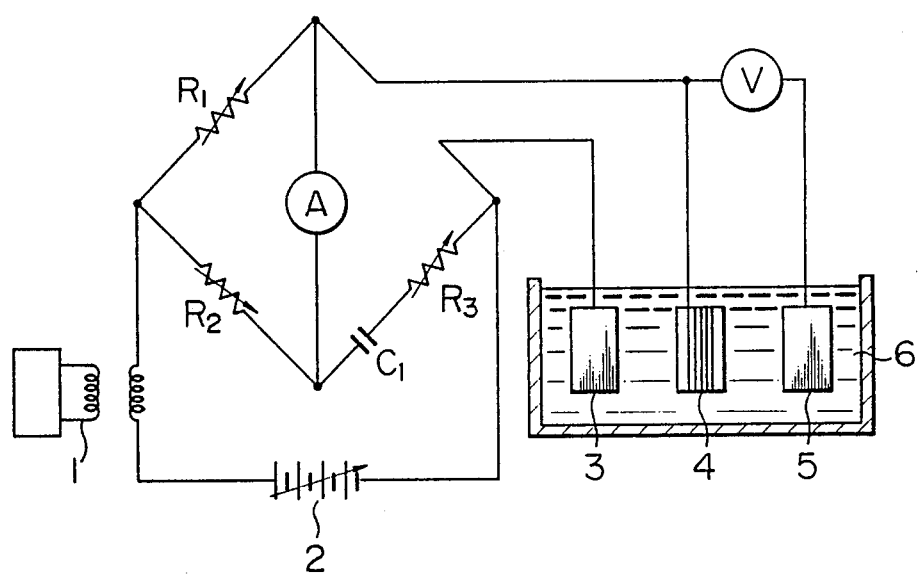
FIG. 4 shows an example of an apparatus for measuring the capacity of the electrical double layer as used in Example 11 mentioned below. The numbers and letters in the Figure indicate the following.
 1. Oscillator
 2. Constant-voltage power source
 3. Platinum electrode
 4. Carbon fiber electrode
 5. Ag/AgCl reference electrode
 6. Electrolyte solution
 A Galvanometer
 $C_1$ Condenser
 $R_1$, $R_2$, $R_3$ Resistance
 V Voltmeter

Then, changing the measuring solution to a 0.1M aqueous solution of NaF, the capacity of the electric double layer was measured by using an apparatus as shown in FIG. 4.

The frequency of the oscillator was set at 1.17 KHz, and the electric potential of the carbon fiber electrode was set at +0.6 V by a constant-voltage power source.

The operation was conducted as follows:

1. By changing the resistance of each arm of the bridge circuit, there was obtained the balancing point, at which the reading of the galvanometer may be minimized.

2. From values of $R^1$ $R^2$ and $C^1$, the capacity of the electric double layer, $Cd_1$, was determined according to the following equation:

$$Cd_1 = C_1 \frac{R_2}{R_1}$$

Then, changing the electric potential of the carbon fiber electrode to 0.2 V, the operation of 1. and 2. was repeated.

The difference ($\Delta gm$) between the capacity of the electric double layer at 0.6 V and that at 0.2 V was determined according to the following equation:

$$\Delta gm = \frac{Cd_1 (0.6\ V) - Cd_1 (0.2\ V)}{(\text{Number of } CF \text{ filament, 6000})(\text{length of } CF \text{ electrode, 5 cm})}$$

Results of the measurement are shown in Table 11.

From the results, the following facts may be observed. Under conditions of stronger surface treatment, while the $\Delta gm$ value shows a tendency to remain constant, the ipa increases. Thus, the ipa is highly correlated with the characteristic properties of the composite. Accordingly, when the ipa shows a constant value, the surface condition may be kept constant.

TABLE 11

| Experiment No. | Air oxidation temp. (°C.) | ipa ($\mu$A/cm$^2$) | ILSS (kg/mm$^2$) | Transverse flexural strength (kg/mm$^2$) | $\Delta$qm ($\mu$C/cm) |
|---|---|---|---|---|---|
| 42 | 400 | 0.11 | 4.0 | 5.2 | $5 \times 10^{-3}$ |
| 43 | 600 | 0.19 | 8.6 | 8.7 | 33 |
| 44 | 800 | 0.25 | 8.7 | 9.2 | 39 |
| 45 | 850 | 0.37 | 8.7 | 10.3 | 36 |
| 46 | 900 | 0.46 | 8.2 | 10.0 | 37 |
| 47 | 950 | 0.70 | 7.3 | 8.2 | 34 |

EFFECT OF THE INVENTION

One of the most advantageous features of this invention in practice is that since the potential sweep method enables measurement of the characteristic of a continuous fiber as it is without cutting the fiber, the process control of surface-treatment conditions can be easily conducted by directly incorporating a potential-sweep measuring apparatus into the production line and, further, since the measurement can be conducted without impairing any characteristic of the specimen carbon fiber, the fiber after the measurement can also be used as the final product.

Another feature of this invention is that since measurement by potential sweep is simple, requires no elaborate technique nor special environment, and can be conducted with good reproducibility in a short time, it is very advantageous in process control and product control in plants and thus has a very high practical value; further, according to the method of this invention, no expensive analytical instrument which needs troublesome maintenance is required, and the production process becomes very simple.

By practicing the method according to this invention, it is possible to judge properly and deal quickly with the abnormality of surface state of the product carbon fiber which can be caused, even when the conditions of surface treatment are apparently constant, by variation in starting fibers or carbonization conditions due to some external disturbance.

What is claimed is:

1. A process for producing a carbon fiber, which comprises making a carbon fiber travel through about a 5% aqueous phosphoric acid solution, applying an electric potential in said solution between the carbon fiber serving as a working electrode and a platinum counter electrode provided in the solution, said potential being swept continuously at a +2 or −2 mV/sec constant scanning rate over the range of the standard electrode potentials of said electrolyte solution, said standard electrode potentials being in the range of about −0.2 to 0.8 V with respect to a Ag/AgCl reference electrode, wherein the resulting change in the current intensity, i, is detected continuously to obtain cyclic current-potential curves, in which i is read off at about +0.40 V selected as the standard voltage versus Ag/AgCl reference electrode, and the current intensity per unit area, ipa is calculated, defined by the equation, ipa ($\mu$A/cm$^2$) = i/Total surface area of the carbon fiber tow, in which the total surface area of the tow is calculated from the length of the carbon fiber electrode, weight per unit length of the carbon fiber tow, number of monofilaments and density of the carbon fiber, so that a preceeding surface oxidation step of said carbon fiber is controlled by estimating said ipa and keeping it at a desired constant value to thereby result in a carbon fiber having a substantially constant surface condition.

2. The method of claim 1, wherein the change in the intensity of the electric current produced by potential sweep is measured by using cyclic voltammetry.

3. The method of claim 1, wherein the carbon fiber is brought into contact with conductive rolls outside the electrolyte solution bath to apply a potential to the carbon fiber.

4. The method of claim 1, wherein the carbon fiber is subjected to a surface oxidation treatment before traveling through said electrolyte solution.

* * * * *